United States Patent
Wiese

(12) 
(10) Patent No.: US 6,433,242 B1
(45) Date of Patent: Aug. 13, 2002

(54) PROCESS FOR FRACTIONATING DIBUTENE

(75) Inventor: Klaus-Diether Wiese, Haltern (DE)

(73) Assignee: OXENO Olefinchemie GmbH, Marl (DE)

(*) Notice: Subject to any disclaimer, the term of this patent is extended or adjusted under 35 U.S.C. 154(b) by 0 days.

(21) Appl. No.: 09/505,673

(22) Filed: Feb. 17, 2000

(30) Foreign Application Priority Data

Feb. 17, 1999 (DE) .......................................... 199 06 518

(51) Int. Cl.$^7$ .............................. C07C 5/03; C07C 7/04; C07C 11/02; B01D 3/14
(52) U.S. Cl. .......................... 585/800; 203/99; 203/91; 203/100; 208/144; 585/250
(58) Field of Search .......................... 203/100, 91, 99; 585/800, 250, 16; 208/144

(56) References Cited

U.S. PATENT DOCUMENTS

| | | | |
|---|---|---|---|
| 5,262,015 A | 11/1993 | Berg et al. | |
| 5,292,990 A | 3/1994 | Kantner et al. | |
| 5,849,972 A | * 12/1998 | Vicari et al. | ................ 585/531 |
| 5,912,191 A | * 6/1999 | Nierlich et al. | ............. 568/697 |
| 5,998,685 A | * 12/1999 | Nierlich et al. | ............. 585/329 |

FOREIGN PATENT DOCUMENTS

| | | |
|---|---|---|
| DE | 2 106 252 | 11/1972 |
| DE | 21 39 630 | 2/1973 |
| DE | 23 39 947 | 2/1974 |
| DE | 2 244 373 | 4/1974 |
| EP | 0 684 721 | 11/1995 |
| WO | WO 92/13818 | 8/1992 |
| WO | WO 93/24438 | 12/1993 |

OTHER PUBLICATIONS

H. Bahrmann, Y. Falbe, New Syntheses with Carbon Monoxide, pp. 372–413, "Koch Reactions", 1980.
R.H. Friedlander, et al., Hydrocarbon Processing, pp. 31–33, "Make Plasticizer Olefins Via N–Butene Dimerization", Feb. 1986.
G. Huebner, Fette•Seifen•Anstrichmittel, vol. 68, No. 4, pp. 290–292, "Vinylierrung Hoeherer Carbonsaeuren An Katalysatorschmelzen", 1966.
B.L. Wadey, et al., Journal of Vinyl Technology, vol. 12, No. 4, pp. 208–211, "The Nonyl Phthalate Ester and Its Use in Flexible PVC", Dec., 1990.
Encycl. Polym. Sci. Eng., vol.17, pp. 426–434, "Vinyl Ester Polymers".
Handbook of Chemistry and Physics, 67th Ed., pp. C–309, C–384, C–308, "Physical Constants of Organic Compounds", 1986–1987.
Ullmanns Encyklopaedie der Technischen Chemie, vol. 19, pp. 368–374, "Polyvinylverbindungen".

* cited by examiner

*Primary Examiner*—Virginia Manoharan
(74) *Attorney, Agent, or Firm*—Oblon, Spivak, McClelland, Maier & Neustadt, P.C.

(57) ABSTRACT

The invention relates to a process for separating dibutenes into an n-octene-containing fraction and a dimethylhexene-containing fraction. The fractions can be processed further separately to the corresponding $C_9$ carboxylic acids and $C_9$ alcohols (isononanols). Successor products of the $C_9$ carboxylic acids include, for example, vinyl esters. Successor products of the $C_9$ alcohols include plasticizers.

15 Claims, No Drawings

PROCESS FOR FRACTIONATING DIBUTENE

BACKGROUND OF THE INVENTION

1. Field of the Invention

The invention relates to a process for fractionating a dibutene mixture and to the use of the dibutene fractions.

2. Discussion of the Background

Dibutene is the term used for mixtures of isomeric $C_8$ olefins obtained by dimerizing n-butenes or $C_4$ streams containing n-butene. For this purpose it is particularly advantageous to employ the so-called raffinate II or raffinate III, which are inexpensively obtained from the processing of crude $C_4$ cuts.

In order to obtain raffinate II or III, butadiene is removed from crude $C_4$ cuts in a first step. This is done either by extracting the butadiene or selectively hydrogenating it to the linear butenes. Both cases produce a virtually butadiene-free $C_4$ cut, which is raffinate 1. In the second step, isobutene is removed from the $C_4$ stream by, for example, reacting it with methanol to prepare methyl tert-butyl ether (MTBE). MTBE is a sought-after motor fuel component. Other options are to react the isobutene from the raffinate I with water to give TBA (tertiary butanol) or to subject the isobutene to acid-catalyzed oligomerization to form diisobutene. The now isobutene-free $C_4$ cut, raffinate II, desirably contains the linear butenes and possibly butanes. As an option, it is also possible to separate off the 1-butene by distillation; if this is done, the cut that is free from 1-butene is referred to as raffinate III.

For the preparation of di-n-butene, either raffinate II or raffinate III can be employed. The use of other industrial $C_4$ streams, such as those from Fischer-Tropsch olefins, for example, is possible. The critical feature is that essentially only linear butenes are present in the feedstock.

The oligomerization of such n-butene-containing $C_4$ streams to mixtures that contain essentially $C_8$ olefins is known in principle; there are three process variants, which are described below.

The oligomerization over acidic catalysts (process A) has been known for a long time, and, in industry, for example, zeolites or phosphoric acid on supports are employed. This process produces isomer mixtures of branched olefins which constitute primarily dimethylhexenes (WO 92/13818). A process which is likewise carried out worldwide is the oligomerization with soluble Ni complexes, known as the DIMERSOL process (process B) (B. Cornils, W. A. Herrmann, Applied Homogenous Catalysis with Organometallic Compounds, page 261–263, Verlag Chemie 1996). Finally, mention should also be made of the oligomerization over nickel fixed-bed catalysts, such as, for example, the process of OXENO-GmbH. The process has entered the literature as the OCTOL process (process C) (Hydrocarbon Process., Int. Ed. (1986) 65 (2. Sect. 1), page 31–33).

The dibutenes obtained by the above-noted processes are prized starting materials in the chemical industry. For example, it is possible by hydroformylation to obtain aldehydes which are longer by one carbon atom—in the case of dibutene, $C_9$ aldehydes—which in turn are further employed for important industrial products. Examples include the hydrogenation of the aldehydes to give alcohols and their reaction with carboxylic acids to give esters. For instance, the acidification of the alcohols with phthalic anhydride leads to diisononyl phthalates, which are highly prized plasticizers in the plastics processing industry. Also important and carried out industrially is the oxidation of the aldehydes to the corresponding carboxylic acids, which are reacted inter alia to give oil-soluble metal salts. These salts are employed, for example, as drying accelerators for coatings (siccatives), or as stabilizers for PVC.

Another exemplary industrial application is the strong-acid-catalyzed reaction of olefins (dibutenes) with carbon monoxide and water to give the carboxylic acids that are longer by one carbon atom, which has entered the literature under the name KOCH reaction. In this case, tertiary branched carboxylic acid mixtures are obtained which, because of their branched nature, are in turn highly suitable for producing the abovementioned metal salts. A particularly important use of the tertiary carboxylic acids is the reaction with acetylene to give vinyl esters, which are used as comonomers for the internal plasticization of polymers. Copolymers of vinyl esters of tertiary carboxylic acids with vinyl acetate, for example, are the basis for environmentally friendly water-dispersible paints and coating materials, and energy-saving thermal insulation renders in buildings.

Dibutene is not a uniform substance but rather is a mixture of many structural isomers which in turn are composed of virtually all the double-bond isomers in different proportions, with many of the double-bond isomers also exhibiting a cis/trans isomerism. Depending on the production process, these constitutional and configurational isomers can be present in different proportions.

When dibutene is prepared from raffinate II or III, the product contains olefin mixtures of essentially unbranched, singly branched and doubly branched substructures. The information given below in the table is only a guide, since varying proportions of the individual structural groups are obtained depending on the process conditions.

One measure of the degree of branching is the iso index, which is easily determined by those skilled in the art. It is defined by the number of branchings per molecule. Accordingly, linear octenes (n-octenes) have an iso index of 0, methylheptenes an iso index of 1 and dimethylhexenes an iso index of 2. The calculation of the iso index of mixtures must take account of the mass fractions of the individual groups of compounds.

TABLE 1

Typical structure distribution in dibutenes, each from different preparation processes, starting from raffinate III.

|  | A Zeolite catalysis | B Dimersol | C Octol |
| --- | --- | --- | --- |
| n-Octene | ~0% | ~6% | ~13% |
| 3-Methylheptenes | ~5% | ~59% | ~62% |
| 3,4-Dimethylhexenes | ~70% | ~34% | ~24% |
| Other $C_8$ olefins | ~25% | ~1% | ~1% |
| Iso index | >1.9 | ≅1.29 | ≅1.12 |

If instead of raffinate II or raffinate III other isobutene-containing $C_4$ cuts are used, such as raffinate I, there is also formation of a host of further, even more highly branched structures, essentially trimethylhexenes such as 2,2,4-trimethylpentenes, 2,2,3-trimethylpentenes, 2,3,4-trimethylpentenes, 2,3,3-trimethylpentenes, etc. Such dibutenes, with an iso index of more than 2, are also known by the name "codibutylene".

The performance properties of the products produced from dibutene are often dependent on the composition and, especially, on the degree of branching of the olefin employed. This may take on very extreme forms, as is evident from the examples below.

An important field of use of dibutenes is the preparation of $C_9$ alcohols which in turn are esterified with carboxylic acids. For instance, dibutene produces isononanol mixtures, which are esterified with phthalic anhydride to give isononyl phthalates: these are employed as plasticizers in plastics.

The degree of branching of the isononyl chains of the phthalates is closely related to the degree of branching of the olefin employed, so that the properties of the phthalates are significantly co-determined by the structure of the olefin mixture that is employed.

TABLE 2

Comparison of typical dynamic viscosities of nonyl phthalates employed industrially.

| Crude material | Oligomerization process | Hydro-formylation process | Viscosities of the isononyl phthalates (20° C.) |
|---|---|---|---|
| Raffinate | A | Co-HP | ≅165 mPa s |
| Raffinate II or III | A | Co-HP | 116–120 mPa s |
| Raffinate II or III | B or C | Co-HP | 70–85 mPa s |
| Raffinate II or III | B or C | Rh-HP | 90–100 mPa s |

Wherein:
 Co-HP: Classic cobalt high-pressure process, 200–300 bar, 140–180° C.; and
 Rh-HP: Rhodium high-pressure process, 150–300 bar, 120–130° C., is unmodified or triphenylphosphine oxide-modified rhodium catalyst.

Other performance properties of the plasticizers are similarly heavily dependent on their degree of branching. Wadey et al. in J. Vinyl Tech. (1990) 208–211 show the marked dependency of the plasticizer properties of dinonyl phthalates on the degree of branching of the nonyl radical.

The vinyl esters of tertiary carboxylic acids, which are frequently employed as a comonomer in the polymerization of vinyl acetates, are another example of the dependency of the plasticizer properties of a compound on its degree of branching. One measure of the plasticizing action of the comonomer is the glass transition point Tg (° C.) of the homopolymer. For an identical empirical formula, the glass transition point can vary across a whole range depending on the structure of the olefin employed. For vinyl esters of $C_9$ carboxylic acids, for example, the literature gives:

TABLE 3

(H. P. H. Scholten, J. Vermeulen, W. J. van Westrenen, Recent Developments in Latices based on Vinyl Esters of branched Monocarboxylic Acids, Seventh International Conference Water-Borne Coatings, London 1987; *W. Lau, VeoVa, a Vinyl Ester Monomer, Polymers Dotcom Magazine, 2(2), February 1996).

| Base olefin | Vinyl esters (VE) of | Tg (° C.) |
|---|---|---|
| 2,3,4-Trimethylpentene | 2,3-Dimethyl-2-isopropylbutanoic acid | 119 |
| 2,2,3-Trimethylpentene | 2-Ethyl-2,3,3-trimethylbutanoic acid | 115 |
| Diisobutene | commercially available vinyl ester | 70 (60)* |
| 2,2,4-Trimethylpentene | 2,2,4-Tetramethylpentoic acid | 55 |
| 2,4-Dimethylhexene | 2,2,4-Trimethylhexanoic acid | 10 |

With plasticizers therefore, an important factor is generally a very low degree of branching of the initial olefins, as demonstrated using the example of the phthalates and vinyl esters.

This does not mean, however, that more highly branched olefins are worthless—what is critical is the correct choice of application. For example, metal salts of highly branched carboxylic acids obtained from olefins with correspondingly high degrees of branching are, owing to the shielding of the polar carboxyl group, particularly soluble in oil and therefore particularly suitable for use for producing siccatives and PVC stabilizers. A general field of use for highly branched olefins is that of acid-catalyzed reactions, such as, for example, the acid-catalyzed alkylation of phenols. In such reactions, highly branched olefins can be used to give much better yields than with linear olefins or olefins with lower degrees of branching, since the former are able to develop tertiary carbenium ions with particular ease.

The great economic importance of the dibutenes and their successor products, and the heavy dependency of their performance properties on structure, therefore, suggested separation of the dibutene mixture.

Separation of the dibutene mixture by distillation, however, is possible only on an analytical scale—and even then not completely—owing to the small differences in boiling point. Distillative separation is therefore not economic. To illustrate this it may be noted that, within the boiling range of dibutene, which is from 104 to 125° C. under atmospheric pressure, about 40 components have been detected to date.

On the industrial scale, therefore, $C_8$ olefins are separated using various other processes, such as adsorption processes, distillation with azeotrope formers, or separation processes with upstream isomerization steps.

U.S. Pat. No. 5,262,015 describes the separation of 1-octene from other $C_8$ olefin isomers by azeotropic distillation using an azeotrope former. Examples of azeotrope formers used are ethyl acetate and amyl methyl ether. However, this process only makes it possible to separate 1-octene, which is present in a large excess, and requires the use of one part of azeotrope former to one part of isomer mixture. In dibutene, on the other hand, the proportion of 1-octene is very low: the double bonds present are predominantly internal. The industrial application of this process to the separation of dibutene is therefore not an option.

U.S. Pat. No. 5,292,990 describes the separation of $C_8$ olefin mixtures by way of the different adsorption/desorption behavior of the isomers on specific zeolites. This process requires highly specific zeolites which are difficult, if not impossible, to obtain commercially, quite aside from the fact that the use of such processes is generally directed to analytical separation techniques. An industrial application is therefore not an option or at the very least is highly complex and uneconomic.

Another possibility of obtaining dibutene mixtures with a relatively low isomer fraction consists in theory in the isomerization of the dibutenes prior to the actual separation process. One example of such a process is given by EP 0684721. The aim of the isomerization is to transform certain isomers into other isomers that are more thermodynamically stable under the chosen conditions, and thus to simplify subsequent separation. In general, however, more highly substituted olefins and/or internal olefins are more thermodynamically stable, so that the olefins with a lower degree of substitution, and/or terminal olefins, which are important for numerous purposes, are lost. Direct separation of the isomer mixture to give the desired structures is therefore not possible industrially by means of combined isomerization/separation processes.

In summary, it is found that the literature contains no industrially applicable and economic method of separating dibutene mixtures.

The properties of individual dibutene isomers, like their boiling points, are often very similar. Substantial separation into individual isomers is therefore virtually impossible, but is also not absolutely necessary economically. In contrast, it would be desirable to obtain (without complex apparatus and with minimum energy consumption) olefin mixtures that are suitable for the preparation of products having defined properties.

SUMMARY OF THE INVENTION

It is an object of the invention to develop a process for separating dibutene mixtures.

This object and other objects have been achieved by the present invention, which provides a process for separating dibutenes into an n-octene-containing fraction having an iso index of less than 90% of the iso index of the original dibutenes, and a dimethylhexene-containing fraction having more than 110% of the iso index of the original dibutenes.

By means of the process of the invention, it is possible to prepare dibutene fractions and to pass on the individual fractions for specific further processing. In comparison to the successor products of the dibutene mixture, the successor products of the individual fractions have defined and durably improved properties.

DESCRIPTION OF THE PREFERRED EMBODIMENTS

Various other objects, features and attendant advantages of the present invention will be more fully appreciated as the same becomes better understood from the following detailed description, which is not intended to be limiting thereof unless otherwise specified.

Preferably, the process of the present invention fractionates dibutenes by separation into a virtually n-octene-free fraction (iso index higher than that of the original dibutenes), which therefore contains branched olefins, and into a second fraction (iso index lower than that of the original dibutenes), which in addition to virtually all the unbranched and singly branched olefins contains only small amounts of more highly branched olefins, takes place successfully in a single step.

Table 4 shows by way of example the isomer distribution of a typical dibutene sample produced by oligomerization of raffinate III in accordance with the Octol process, together with the associated mass fractions. As a measure of the boiling points, some of which are unknown, the retention indices are indicated, which were determined by gas chromatography and measured against squalene. The stated retention indices represent a boiling range from about 105 to 126° C. The small differences in the retention indices are an indication of very small differences in boiling point between the isomers. In addition, components with higher and lower degrees of branching alternate unsystematically in the sequence.

TABLE 4

Boiling point data from Handbook of Chemistry and Physics, 67th Ed., 1986–1987, CRC Press (the entire contents of which being hereby incorporated by reference).

| No. | Retention index based on squalene b.p. | Isomer | Mass fraction of the isomers |
|---|---|---|---|
| 1 | 725.4 105.1° C. | 4,4-Dimethyl-1-hexene | 0.17% |
| 2 | * | cis-2,4-Dimethyl-3-hexene | ** |
| 3 | 728.0 | trans-2,4-Dimethyl-3-hexene | 0.07% |

TABLE 4-continued

Boiling point data from Handbook of Chemistry and Physics, 67th Ed., 1986–1987, CRC Press (the entire contents of which being hereby incorporated by reference).

| No. | Retention index based on squalene b.p. | Isomer | Mass fraction of the isomers |
|---|---|---|---|
| 4 | 730.7 | 2,4-Dimethyl-2-hexene | 0.14% |
| 5 | 733.7 | 2-Methyl-3-ethyl-1-pentene | 0.05% |
| 6 | 734.7 | trans-4,5-Dimethyl-2-hexene | 0.08% |
| 7 | 736.0 | cis-4,5-Dimethyl-2-hexene | 0.08% |
| 8 | 738.3 | cis-5-Methyl-3-heptene | 1.13% |
| 9 | 740.1 | 3-Methyl-1-heptene | 0.71% |
| 10 | 741.0 | trans-5-Methyl-3-heptene | 6.37% |
| 11 | 749.6 | 3-Methyl-2-ethyl-1-pentene | 0.93% |
| 12 | 752.0 | trans-3,5-Dimethyl-2-hexene | 0.37% |
| 13 | 752.3 | cis-3,5-Dimethyl-2-hexene | 0.10% |
| 14 | 755.7 | cis-3,4-Dimethyl-2-hexene | 4.69% |
| 15 | 760.0 | trans-3,4-Dimethyl-2-hexene | 14.41% |
| 16 | 767.6 | trans-5-Methyl-2-heptene | 9.62% |
| 17 | 775.9 | cis-5-Methyl-2-heptene | 3.56% |
| 18 | 777.1 | trans-3,4-Dimethyl-3-hexene | 2.99% |
| 19 | 777.6 | cis-3-Methyl-3-heptene | 5.21% |
| 20 | 779.1 120.0° C. | 2-Ethyl-1-hexene | 1.07% |
| 21 | 781.9 121.3° C. | 1-n-Octene | 0.10% |
| 22 | 782 .9 | cis-3,4-Dimethyl-3-hexene | 2.79% |
| 23 | 784.1 | trans-3-Methyl-3-heptene | 9.77% |
| 24 | *122.3° C. | trans-4-n-Octene | 3.06% |
| 25 | 786.6 122.5° C. | cis-4-n-Octene | 0.67% |
| 26 | 790.8 | 2,3-Dimethyl-2-hexene | 0.10% |
| 27 | 788.3 | cis-3 -Methyl-2-heptene | 6.58% |
| 28 | *122.9° C. | cis-3-n-Octene | 1.11% |
| 29 | 789.1 123.3° C. | trans-3-n-Octene | 5.08% |
| 30 | 798.8 | trans-3-Methyl-2-heptene | 11.30% |
| 31 | *125.0° C. | trans-2-n-Octene | 5.10% |
| 32 | 802.0 125.6° C. | cis-2-n-Octene | 1.88% |
|  | Remainder | Alkanes and unknowns | 0.71% |

*The retention indices lie between the adjacent values. They could not be determined precisely owing to superimposed peaks;
**Traces.

Nevertheless, separation by means of the process of the invention is successful, preferably by a distillative cut between compounds 15 and 16 of Table 4.

For the purpose of distillative separation, the small differences in boiling point between the isomers necessitate a column having an appropriately high separation efficiency, or the required number of theoretical plates. This is preferably achieved by incorporating column trays, perforated plates or packings such as Raschig rings, wire meshes or dumped packings. On the basis of their high separation efficiency at low differential pressure, particular preference is given to mesh packings, such as CY packings from Sulzer, for example.

Complete, isomerically pure separation of the dibutene is unnecessary for many of its successor products in practice, fractionation into a fraction predominantly containing olefins with low degrees of branching (iso index less than 90% of that of the original dibutenes) and into a fraction predominantly containing olefins with higher degrees of branching (iso index greater than 110% of that of the original dibutenes) has been found to be entirely adequate.

The iso index of the n-octene-containing fraction is preferably below 1.0 and in particular preference below 0.9. This means in both cases that the iso index of the dimethylhexene-containing fraction is greater than the iso index of the original dibutenes (starting olefin).

The fractionation of the dibutenes in the process of the invention is preferably carried out by means of continuous distillation. The distillation can be performed within a wide pressure range, i.e., both under reduced-pressure conditions and under superatmospheric pressure conditions. However, distillation at atmospheric pressure is more preferred in order to keep the technical complexity low.

In the process of the invention, the n-octene-containing fraction is obtained as the bottom product. This fraction has a boiling range of preferably from 110 to 126° C., particularly preferably from 115 to 123° C., under atmospheric pressure.

The dimethylhexene-containing fraction, on the other hand, is obtained as the top product. The top product preferably has a boiling range under atmospheric pressure of from 95 to 120° C., more preferably from 105 to 115° C.

The boiling ranges indicated are pressure dependent. If the process of the invention is operated at different pressures, then the preferred boiling ranges must be converted accordingly.

The dibutene fractions produced with the process of the invention can be employed in subsequent reactions in which the untreated dibutene mixture is also customarily used. These include acid-catalyzed reactions such as the KOCH synthesis to give tertiary carboxylic acids and the subsequent use thereof to prepare vinyl esters, or the alkylation of benzenes and phenols, and also the metal-catalyzed preparation of aldehydes by hydroformylation, and the further processing of these aldehydes to these corresponding alcohols and the plasticizers derived from them, and, still further, the oxidation of the aldehydes obtained by hydroformylation, to give non-tertiary carboxylic acids.

The n-octene-containing bottom fraction, with a low degree of branching, is preferably employed, for example, when the intention is to produce readily biodegradable products. As is known, alkyl chains with low degrees of branching are more readily biodegradable than those with higher degrees of branching.

Furthermore, the low level of branching of the bottom product is of particular advantage when the successor products are plasticizers. For example, a less highly branched isononyl is obtained by hydroformylating the bottom fraction with its low degree of branching than when using the unseparated mixture. This, following esterification with phthalic anhydride, for example, gives a plasticizer having markedly improved properties (see comparative examples).

The dibutene fractions obtained in accordance with the invention (n-octene-containing and/or dimethylhexene-containing fraction) can be used to prepare isononanols and/or their esters. The isononanols are prepared, for example, by hydroformylating the dibutenes to the corresponding aldehydes and then hydrogenating them. The hydroformylation can be carried out as desired with cobalt catalysts or rhodium catalysts. A preferred example includes cobalt-catalyzed reaction systems in which cobalt salts are reacted in aqueous solution with synthesis gas ($H_2$:CO in a volume ratio of 1:1) to give cobalt hydridocarbonyls. These cobalt complexes catalyze the reaction of the olefins with synthesis gas to the corresponding oxo aldehydes. The oxo aldehydes are subsequently hydrogenated to the desired alcohols. These processes are known and are described, for example, in DE-A 21 39 630, DE-A 21 06 252, DE-A 22 44 373 or WO 93/24438, the entire contents of each of which are hereby incorporated by reference.

Preferably, the hydroformylation is conducted with a reaction temperature of from 50 to 200° C. and a synthesis gas pressure of from 100 to 400 bar. The olefin, with or without an alcohol as solubilizer, is used simultaneously as starting material and solvent. Following hydroformylation, the catalyst is destroyed by oxidation, the aqueous phase is separated from the product mixture, the unreacted olefins are returned to the hydroformylation stage, and the resulting oxo aldehydes are hydrogenated to the corresponding isononanols. Their further processing to give the diisononyl phthalates takes place by esterification with phthalic anhydride, with catalysis by butyl titanates.

Another preferred use of the dibutene fractions prepared by the process of the invention (n-octene-containing and/or dimethylhexene-containing fraction) is the preparation of nonanoic acids and/or their vinyl esters. For this purpose, the respective olefin fraction is first of all reacted with carbon monoxide in the presence of strong acids such as sulfuric acid or boron fluoride hydrates to give tertiary carboxylic acids. The tertiary carboxylic acids are then reacted with acetylene in the presence of the zinc salt of the carboxylic acids (Encycl. Polym. Sci. Eng. 17, pp. 426–434) as catalyst to give the corresponding vinyl esters, or the latter are obtained by transesterification with vinyl acetate (Ullmann, 4th edition, volume 19, pp. 368 ff.). The entire contents of both of the aforementioned references are hereby incorporated by reference. These esters are used as copolymers for example, for the preparation of modified polyvinyl acetate, where they bring about internal plasticization while at the same time increasing the stability to hydrolysis. Here again, the use of the bottom fraction with its low degree of branching achieves a very substantial improvement in the plasticine properties, as shown by the examples.

The top fraction, which contains highly branched isomers, on the other hand, is employed with particular advantage when rapid biological breakdown is not required or when particularly high oil solubility is a factor. Both of these apply in a particularly high measure to the metal salts of branched carboxylic acids, which are used as drying. accelerators in paints and coatings. In this case, higher oil solubility means that higher concentrations of the metal salt in the organic medium can be obtained. Since the paints and coatings are intended to protect the substrate, a long service life without the addition of toxic agents is of essential importance.

These branched carboxylic acids can be obtained from the top fraction either by hydroformylating and oxidizing the resultant aldehydes or, preferably, by hydrocarboxylation. One example of an appropriate process in this case is the KOCH synthesis, as described in Falbe, New Synthesis with Carbon Monoxide, Springer Verlag, Berlin 1980, p. 372, the entire contents of which being hereby incorporated by reference. Under the chosen reaction conditions, the more highly branched olefins of the dimethylhexene-containing fraction give stable Markovnikov products, i.e., predominantly tertiary carboxylic acids.

The dibutene fractions prepared in accordance with the present process, especially the top fraction containing branched olefins, are highly suitable for acid-catalyzed reactions where carbenium ions play the part of an intermediate, since these ions are formed with particular readiness from branched olefins. As a general rule, such reactions then take place with improved selectivity as compared with the use of olefins with little or no branching.

Furthermore, following hydrogenation, the dimethylhexene-containing fraction can be used as a gasoline component with a high octane number.

EXAMPLES

Having generally described this invention, a further understanding can be obtained by reference to certain specific examples, which are provided herein for purposes of illustration only and are not intended to be limiting unless otherwise specified.

Example 1
Dibutene Fractionation

An industrial dibutene mixture with a composition in accordance with Table 4 was fractionated. The column used had the following technical data:

| | |
|---|---|
| Total length | 27.5 m |
| Diameter | DN 300 |
| Mesh packings | Sulzer CY (about 10 theoretical plates per meter) |
| Packed length | 18.72 m. |

In all, 117 elements of the mesh packings were installed on 9 support grids. The distribution of steam within the column took place by 9 tube distributors and 8 liquid collectors. The typical operating conditions were:

| | |
|---|---|
| Inflow | 100 1/h |
| Distillate | ~30 1/h |
| Bottom discharge | ~70 1/h |
| Return flow | ~700 1/h |
| Column-top temperature | 114° C. |
| Bottom temperature | 124° C. |
| Pressure difference | ~160 mbar. |

Distillate offtake, inflow and return flow were volume-controlled and the bottom discharge was operated with level-control. Since the inflow came directly from an industrial plant and, consequently, there were slight fluctuations in the concentrations, the top and bottom discharges were continually analyzed by gas chromatography and the inflow was altered accordingly. Components 15 and 16 of the mixture were used as reference components for this purpose. The column was operated in such a way that component 15 (trans-3,4-dimethyl-2-hexene) was, as far as possible, completely present in the distillate, component 16 (trans-5-methyl-2-heptene) on the other hand present as far as possible completely in the bottom phase.

The column was tested in pilot operation lasting 150 days. In the course of this test it was found that even under industrial conditions it is possible to operate the column reproducibly. After the conclusion of pilot operation, the collected top and bottom fractions were again analyzed by gas chromatography, the resultant olefins being hydrogenated directly in the injection block of the gas chromatograph. In this way a cumulative analysis is obtained. The analysis of the feedstock, which changes slightly during this period, is of course an exemplary individual analysis.

The results obtained were as follows:

TABLE 5

| | Cumulative analysis | | |
|---|---|---|---|
| | Starting material | Bottom product | Top product |
| n-Octene | 16.8% | 24.0% | <0.1% |
| 3-Methylheptenes | 56.5% | 65.3% | 29.1% |
| 3,4-Dimethylhexenes | 24.7% | 10.0% | 63.5% |
| 2,3-Dimethylhexenes | 0.64% | <0.1% | 1.6% |
| 3,3-Dimethylhexenes | 0.27% | <0.1% | 1.0% |
| 2,4-Dimethylhexenes | 0.67% | <0.1% | 2.5% |
| Other C$_8$ olefins | 0.43% | 0.7% | 2.3% |
| Iso index | ≅1.18 | 0.87 | ≅1.71 |

Examples 2 to 4
Preparation of Tertiary Carboxylic Acids

Unfractionated dibutene (Example 2), the dimethylhexene-containing fraction prepared in accordance with the invention (top product, Example 4), and the n-octene-containing fraction prepared in accordance with the invention (bottom product, Example 3) were reacted in accordance with DE 23 39 947 (the entire contents of which being hereby incorporated by reference) to give tertiary carboxylic acids. The catalyst used was a complex containing boron fluoride and water, with Cu$^+$ as cocatalyst. The reactions took place in a stirred autoclave within a temperature range of 20–35° C. and under a CO pressure of 30 bar. The pressure was held constant by metering in further CO. The reaction was ended as soon as uptake of CO was no longer observed.

Separation of the catalyst phase, water scrubbing and distillative work-up of the crude carboxylic acids gave products of the following composition (figures in % by mass).

TABLE 6

| Product | Example 2 Carboxylic acid A | Example 3 Carboxylic acid B | Example 4 Carboxylic acid C |
|---|---|---|---|
| 2,2-Dimethylheptanoic acid | 7.31 | 2.30 | 8.17 |
| 2-Methyl-2-ethyl-hexanoic acid | 54.3 | 21.7 | 71.0 |
| 2-Methyl-2-propylpentanoic acid | 7.09 | 3.62 | 6.99 |
| 2,2-Diethylpentanoic acid | 3.40 | 2.02 | 2.54 |
| 2,2,5-Trimethylhexanoic acid | 0.83 | 1.71 | 0.09 |
| 2,2,4-Trimethylhexanoic acid | 0.81 | 2.13 | 0.18 |
| 2,4-Dimethyl-2-ethylpentanoic acid | 1.76 | 4.44 | 0.30 |
| 2,2,3-Trimethylhexanoic acid | 2.54 | 7.10 | 0.74 |
| 2-Methyl-2-isopropylpentanoic acid | 5.44 | 11.4 | 1.97 |
| 2,3-Dimethyl-2-ethylpentanoic acid A | 7.27 | 18.9 | 3.40 |
| 2,3-Dimethyl-2-ethyl-pentanoic acid B | 7.59 | 20.1 | 3.54 |
| 2-Ethyl-2-isopropylbutanoic acid | 1.19 | 3.45 | 0.55 |
| Other, unknown acids | 0.50 | 1.13 | 0.48 |

Examples 5 to 7

The mixtures of tertiary carboxylic acids obtained in Examples 2 to 4 were reacted with acetylene at atmospheric pressure at a temperature of 190–220° C. in the presence of the zinc salt of the respective acids to be reacted, in accordance with the equation:

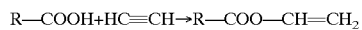

$$R\!-\!COOH + HC\!\equiv\!CH \rightarrow R\!-\!COO\!-\!CH\!=\!CH_2$$

The reaction was conducted in accordance with the method of G. Hübner, Fette, Seifen, Anstrichmittel, 68, (4), pp, 290–292 (1966), the entire contents of which are hereby incorporated by reference.

Following distillation, vinyl esters were obtained with a purity of >=99.8%, and according to analysis by gas chromatography these esters had essentially the same isomer composition as the carboxylic acids employed, these esters are referred to below as vinyl ester A (based on dibutene as such, precursor-carboxylic acid A), vinyl ester B (based on bottom product of the distillation of Example 1, precursor-carboxylic acid B), and vinyl ester C (based on top product of the distillation, Example 1, carboxylic acid C).

Examples 8 to 12

Homopolymers were prepared from the vinyl esters of Examples 5 to 7 in accordance with the following standard procedure (Examples 10 to 12) and their glass transition point was determined as a measure of their suitability as copolymers for internal plasticization.

Starting Materials

| | Parts by weight |
|---|---|
| Monomer | |
| Vinyl ester of a tertiary $C_9$ or $C_{10}$ carboxylic acid | 100.00 |
| Aqueous phase | |
| DI water | 70.00 |
| Anionic surfactant, e.g., Marlon ® A 390 (85% active substance) | 0.03 |
| Nonionic surfactant, e.g., Marlon ® 820 (25% strength solution) | 8.00 |
| Potassium peroxodisulfate ($K_2S_2O_8$) | 0.10 |
| Potassium carbonate | 0.25 |
| Hydroxyethylcellulose, e.g., Natrosol 250 L (or LR) | 2.00 |
| Acetic acid (100%) | 0.20 |
| Initiator solution | |
| Potassium peroxodisulfate | 0.23 |
| DI water | |

Procedure

The aqueous phase and about 10% of the monomer were heated with stirring to 75° C. After 15 minutes at this temperature, the remainder of the monomer and the initiator solution were metered in separate streams. The monomer was added at a uniform rate over 120 minutes and the initiator solution over 135 minutes. During the metered additions, the temperature was maintained between 75 and 80° C. After a further 120 minutes of stirring at the same temperature, the batch was cooled to room temperature.

Directly, or following filtration, the resultant emulsion was used to produce moldings of which the glass transition points were determined by torsional vibration analysis in accordance with DIN 53455.

In addition, two commercially customary vinyl esters of known glass transition points were subjected to the same procedure in order to ensure the comparability of the test procedure. These were firstly a vinyl ester of tertiary $C_{10}$ acids (based on tripropene, Comparative Example 8), which is in widespread use as an internal plasticizer for e.g. vinyl acetate (literature glass transition point −3° C.). Secondly, use was made of a vinyl ester of tertiary $C_9$ acids (Comparative Example 9), i.e. a vinyl ester with the same empirical formula but a different degree of branching than the vinyl esters prepared in accordance with the above examples (literature glass transition point in the region of +60° C.).

The measurements gave the following data

TABLE 7

| Example | 8 (comparative) | 9 (comparative) | 10 | 11 | 12 |
|---|---|---|---|---|---|
| Vinyl ester | C10-VE* | C9-VE* | A (Dibutene) | B (Bottom) | C (Top) |
| Glass transition point (° C.) | −3 | +60 | −3 | −12 | +15 |

*commercial vinyl esters based on tertiary $C_9$ and $C_{10}$ carboxylic acids (W. Lau, VeoVa, a Vinyl Ester Monomer. Polymers DotCom Magazine, 2, (2), February 1996), the entire contents of which are hereby incorporated by reference.

Comparative Examples 8 and 9 show that the standard formulation brings results comparable with the literature. In addition, Example 9 shows that normally, with tertiary $C_9$ carboxylic acids, vinyl esters having an extremely high glass transition point are obtained, which are totally unsuitable for internal plasticization.

In contrast, even the vinyl ester based on the dibutene employed (Example 10) shows a plasticizing suitability comparable with the industrially customary product (Comparative Example 8). The vinyl ester based on the bottom product from the dibutene distillation (Example 11) with a glass transition point of −12° C. is by comparison a comonomer having a very substantially improved plasticizing action. Even the product of the branched tertiary carboxylic acids (Example 12; based on top product of the distillation of Example 1) has a substantially lower glass transition point than the comparative product from Example 9. If use as a comonomer for internal plasticization is the parameter, therefore, the product from Example 11 is by far the most suitable in comparison to the products from Examples 8, 9, 10 30 and 12.

The tertiary carboxylic acids of Example 7, on the other hand (carboxylic acid C, based on top product of Example 1), give comonomers which have only a small plasticizing effect (see Example 12). Because of their greater branching, however, they are particularly suitable, for example, for the preparation of oil-soluble metal salts such as drying accelerators for coating materials and stabilizers for PVC or for hydrolysis-stable esters as solvents.

Examples 13 to 15

Phthalate plasticizers were prepared from the fractions of Example 1 in the following way:

The respective olefin fraction (starting material, bottom product and top product) was hydroformylated as known from the literature using synthesis gas ($CO/H_2$~1/1) in the presence of cobalt compounds as catalyst and at about 200 bar of 180° C. From the resultant reaction discharge, the useful products ($C_9$ aldehydes and q alcohols) were separated off by distillation and, again in a known manner, were hydrogenated to the alcohols. The resulting isononanol mixture was finally reacted with phthalic anhydride, in a known manner, to give the corresponding phthalates.

The phthalates were tested for the suitability as plasticizers by measuring their viscosity. For a given empirical formula, the viscosity of the esters decreases as the degree of branching goes up; conversely, the plasticizing properties are improved as the degree of branching falls.

Table 8 clearly shows that from the bottom product of the distillation of Example 1 a particularly good plasticizer is obtained.

The table below indicates the isomer distribution of the known $C_9$ alcohols, which covers about 98% of the total alcohols. The remainder are unresolved other isomers of $C_9$ alcohols. The viscosity relates to the respective phthalate prepared from the alcohol mixture (measured at 20° C.).

TABLE 8

| Example Olefin | 13 Starting material | 14 Bottom | 15 Top |
|---|---|---|---|
| n-Octenes | 17.5% | 25.0% | 0.0% |
| Methylheptenes | 54.7% | 65.0% | 31.0% |
| Dimethylhexenes | 27.7% | 10.0% | 69.0% |

TABLE 8-continued

| Example Olefin | 13 Starting material | 14 Bottom | 15 Top |
|---|---|---|---|
| Isomer distribution of the $C_9$ alcohols | | | |
| n-Nonanol | 8.4% | 12.4% | 0.0% |
| 2-Methyloctanol | 4.6% | 6.4% | 0.0% |
| 2-Ethylheptanol | 2.5% | 3.3% | 0.0% |
| 2-Propylhexanol | 2.0% | 2.9% | 0.0% |
| 4-Methyloctanol | 17.3% | 20.5% | 9.6% |
| 2,3-Dimethylheptanol | 1.8% | 2.2% | 1.2% |
| 3-Ethylheptanol | 7.0% | 8.4% | 4.0% |
| 2-Propyl-3-ethylpentanol | 0.2% | 0.2% | 0.1% |
| 2-Ethyl-4-methylhexanol | 2.5% | 2.8% | 1.5% |
| 2,5-Dimethylheptanol | 8.2% | 9.9% | 4.7% |
| 6-Methyloctanol | 17.5% | 21.0% | 9.9% |
| 4,5-Dimethylheptanol | 22.3% | 8.1% | 55.0% |
| 3-Ethyl-4-methylhexanol | 5.4% | 1.9% | 14.0% |
| Viscosity of the mixture at 20° C. in mPas | 77 | 68 | 103 |

From the bottom product from dibutene distillation, therefore, a plasticizer having a particularly low viscosity is obtained.

This application is based on German patent application DE 19906518.7, filed Feb. 17, 1999, the entire contents of which are hereby incorporated by reference.

Having now fully described this invention, it will be apparent to one of ordinary skill in the art that many changes and modifications can be made thereto without departing from the spirit or scope of the invention as set forth herein.

What is claimed is:

1. A process for fractionating a dibutene mixture, the process comprising:
   separating a dibutene mixture, having an iso index, into two fractions;
   an n-octene-containing bottom fraction having an iso index of less than 90% of said iso index of said dibutene mixture; and
   a dimethylhexene-containing top fraction having an iso index of more than 110% of said iso index of said dibutene mixture, wherein
   said dibutene mixture comprises trans-3,4-dimethyl-2-hexene and trans-5-methyl-2-heptene; and
   said separating comprises taking a distillative cut between the trans-3,4-dimethyl-2-hexene and trans-5-methyl-2-heptene.

2. The process as claimed in claim 1, wherein said n-octene-containing bottom fraction has an iso index of less than 1.0.

3. The process as claimed in claim 1, wherein said n-octene-containing bottom fraction has an iso index of less than 0.9.

4. The process as claimed in claim 1, wherein said separating of said dibutene mixture comprises continuous distillation.

5. The process as claimed in claim 4, wherein said distillation is performed under atmospheric pressure.

6. The process as claimed in claim 1, wherein said n-octene-containing bottom fraction is obtained as a bottom product and said dimethylhexene-containing top fraction is obtained as a top product in said separating.

7. The process as claimed in claim 1, wherein said n-octene-containing bottom fraction has a boiling range of 110 to 126° C. under atmospheric pressure.

8. The process as claimed in claim 1, wherein said n-octene-containing bottom fraction has a boiling range of 115 to 123° C. under atmospheric pressure.

9. The process as claimed in claim 1, wherein said dimethylhexene-containing top fraction has a boiling range of 95 to 120° C. under atmospheric pressure.

10. The process as claimed in claim 1, wherein said dimethylhexene-containing top fraction has a boiling range of 105 to 115° C. under atmospheric pressure.

11. The process as claimed in claim 1, further comprising preparing nonanoic acid from said dimethylhexene-containing top fraction.

12. The process as claimed in claim 1, further comprising preparing isononanol from said dimethylhexene-containing top fraction.

13. The process as claimed in claim 1, further comprising preparing nonanoic acid from n-octene-containing bottom fraction.

14. The process as claimed in claim 1, further comprising preparing isononanol from said n-octene-containing bottom fraction.

15. The process as claimed in claim 1, further comprising hydrogenating said dimethylhexene-containing top fraction to produce a motor fuel component.

* * * * *